(12) United States Patent
Paramasivam et al.

(10) Patent No.: US 9,983,148 B2
(45) Date of Patent: May 29, 2018

(54) SYSTEM AND METHOD FOR PRODUCTION LINE MONITORING

(71) Applicant: KLA-Tencor Corporation, Milpitas, CA (US)

(72) Inventors: Saravanan Paramasivam, Chennai (IN); Martin Plihal, Pleasanton, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 30 days.

(21) Appl. No.: 15/166,819

(22) Filed: May 27, 2016

(65) Prior Publication Data

US 2016/0377552 A1  Dec. 29, 2016

Related U.S. Application Data

(60) Provisional application No. 62/198,917, filed on Jul. 30, 2015.

(30) Foreign Application Priority Data

May 28, 2015 (IN) .............................. 2680CHE2015

(51) Int. Cl.
*G01N 21/95* (2006.01)
*H01L 21/67* (2006.01)
(Continued)

(52) U.S. Cl.
CPC ..... *G01N 21/9501* (2013.01); *G01N 21/8851* (2013.01); *G05B 19/00* (2013.01);
(Continued)

(58) Field of Classification Search
CPC ................ G05B 23/0275; G05B 19/00; G05B 2219/45031; G01N 21/8851;
(Continued)

(56) References Cited

U.S. PATENT DOCUMENTS 8,219,942 B2 * 7/2012 Itoh .......................... G03F 1/86
355/67
2002/0166964 A1 11/2002 Talbot
(Continued)

OTHER PUBLICATIONS

PCT Search Report for International Application No. PCT/US2016/034718 dated Aug. 19, 2016.

*Primary Examiner* — Sang Nguyen
(74) *Attorney, Agent, or Firm* — Suiter Swantz pc llo (57) ABSTRACT

A method for production line monitoring during semiconductor device fabrication includes acquiring a plurality of inspection results from a plurality of reference samples with an inspection sub-system. The method includes storing the acquired inspection results and geometric pattern codes for each of the reference samples in a database. The method includes acquiring an additional inspection result from an additional sample, where the additional inspection result includes an additional set of geometric pattern codes for identifying each defect identified within the additional inspection result from the additional sample. The method also includes correlating the set of geometric pattern codes of the additional sample with the geometric pattern codes from the reference set of samples to identify at least one of one or more new patterns or one or more patterns displaying a frequency of occurrence above a selected threshold.

26 Claims, 9 Drawing Sheets

(51) Int. Cl.
*G01N 21/88* (2006.01)
*G05B 19/00* (2006.01)
*G05B 23/02* (2006.01)
*H01L 21/66* (2006.01)

(52) U.S. Cl.
CPC .... G05B 23/0275 (2013.01); H01L 21/67253 (2013.01); H01L 22/20 (2013.01); *G01N 2021/8858* (2013.01); *G05B 2219/45031* (2013.01); *H01L 22/12* (2013.01)

(58) Field of Classification Search
CPC ........ G01N 21/9501; G01N 2021/8858; H01L 22/20; H01L 21/67253; H01L 22/12
See application file for complete search history.

(56) References Cited

U.S. PATENT DOCUMENTS

| | | |
|---|---|---|
| 2004/0016897 A1 | 1/2004 | Stokowski et al. |
| 2005/0142455 A1* | 6/2005 | Ando .................. G03F 1/84 430/5 |
| 2005/0254699 A1* | 11/2005 | Sano .................. G06T 7/001 382/149 |
| 2007/0069158 A1 | 3/2007 | Ohnishi |
| 2008/0170773 A1* | 7/2008 | Wihl .................. G03F 1/84 382/144 |
| 2008/0196016 A1* | 8/2008 | Todd .................. G06F 9/546 717/143 |
| 2011/0204228 A1 | 8/2011 | Tsuno et al. |
| 2014/0219544 A1 | 8/2014 | Wu et al. |

* cited by examiner

SYSTEM AND METHOD FOR PRODUCTION LINE MONITORING

PRIORITY

The present application claims priority to India Provisional Patent Application No. 2680/CHE/2015, filed May 28, 2015, entitled NEW METHOD FOR PRODUCTION LINE MONITORING USING DESIGN INFORMATION, naming Saravanan Paramasivam and Martin Plihal as inventors; and U.S. Provisional Patent Application No. 62/198,917, filed Jul. 30, 2015, entitled METHOD FOR PRODUCTION LINE MONITORING USING DESIGN INFORMATION, naming Saravanan Paramasivam and Martin Plihal as inventors, both of which are incorporated herein by reference in the entirety.

TECHNICAL FIELD

The present invention generally relates to the inspection of semiconductor wafers during device fabrication, and, more particularly, the systematic monitoring of pattern failures based on design data.

BACKGROUND

Current approaches to production line monitoring during semiconductor device manufacture is based on two approaches. Production line monitoring is often carried out by monitoring defect counts on wafers using statistical process control (SPC) charts to uncover excursions. A second approach includes the manual review of a random sample of 100-200 defects with subsequent renormalization of defect counts per defect type. This is carried out to monitor the population of critical defects on the wafer and to uncover any new defect that may show up in the process. Typical approaches do not allow operators to monitor failure rates in relation to design patterns and fail to effectively tie defectivity to systematic device design and/or integration issues. Therefore, it would be desirable to provide a system and method that cures the shortcomings of current systems as identified above.

SUMMARY

A method for production line monitoring is disclosed. In one embodiment, the method includes acquiring a plurality of inspection results from a plurality of reference samples with an inspection sub-system, each inspection result being acquired from one reference sample of the plurality of reference samples, wherein each inspection result includes a geometric pattern code for each defect identified on the particular reference sample, wherein the geometric pattern code serves to identify the pattern associated with the particular defect. In another embodiment, the method includes storing the acquired inspection results and the associated geometric pattern codes in a database. In another embodiment, the method includes acquiring an additional inspection result from an additional sample, wherein the additional inspection result includes an additional set of geometric pattern codes for identifying each defect identified within the additional inspection result from the additional sample. In another embodiment, the method includes correlating the set of geometric pattern codes of the additional sample with the geometric pattern codes from the reference set of samples to identify at least one of one or more new patterns or one or more patterns displaying a frequency of occurrence above a selected threshold.

A system for production line monitoring is disclosed. In one embodiment, the system includes an inspection sub-system including an illumination source and a detector, wherein the illumination source is configured to generate illumination, wherein the inspection sub-system is configured to scan the illumination from the illumination source across a sample, wherein the detector is configured to detect illumination from the sample. In another embodiment, the system includes a database maintained in memory for storing inspection results acquired from a reference set of samples with the inspection sub-system, wherein each inspection result from the reference set of samples includes a geometric pattern code for each defect identified on the particular reference sample, wherein the geometric pattern code serves to identify the pattern associated with the particular defect. In another embodiment, the system includes an analyzer, the analyzer including one or more processors and memory, wherein the one or more processors are configured to execute a set of program instructions maintained on the memory. In another embodiment, the program instructions are configured cause the analyzer to: receive an additional inspection result from an additional sample from the inspection sub-system, wherein the additional inspection result includes an additional set of geometric pattern codes for each defect identified within the additional inspection result from the additional sample; retrieve the inspection results acquired from the reference set of samples including the geometric pattern code for each defect identified on the particular reference sample from the database; and correlate the set of geometric pattern codes of the additional sample with the geometric pattern codes from the reference set of samples to identify at least one of one or more new patterns or one or more patterns displaying a frequency of occurrence above a selected threshold.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention

BRIEF DESCRIPTION OF THE DRAWINGS

The numerous advantages of the disclosure may be better understood by those skilled in the art by reference to the accompanying figures in which.

DETAILED DESCRIPTION OF THE INVENTION

Reference will now be made in detail to the subject matter disclosed, which is illustrated in the accompanying drawings.

Referring generally to FIGS. 1A-3C, systems and methods for production line monitoring are described in accordance with the present disclosure.

Embodiments of the present disclosure are directed to the monitoring of the stability of a semiconductor device manufacturing process with respect to pattern failures in specific design locations. Additional embodiments of the present disclosure are directed to the collection of inspection signals and the correlation of those signals to design data, allowing systematic failures, such as failures in device design or integration, to be separated from random defectivity.

Figure 1A:
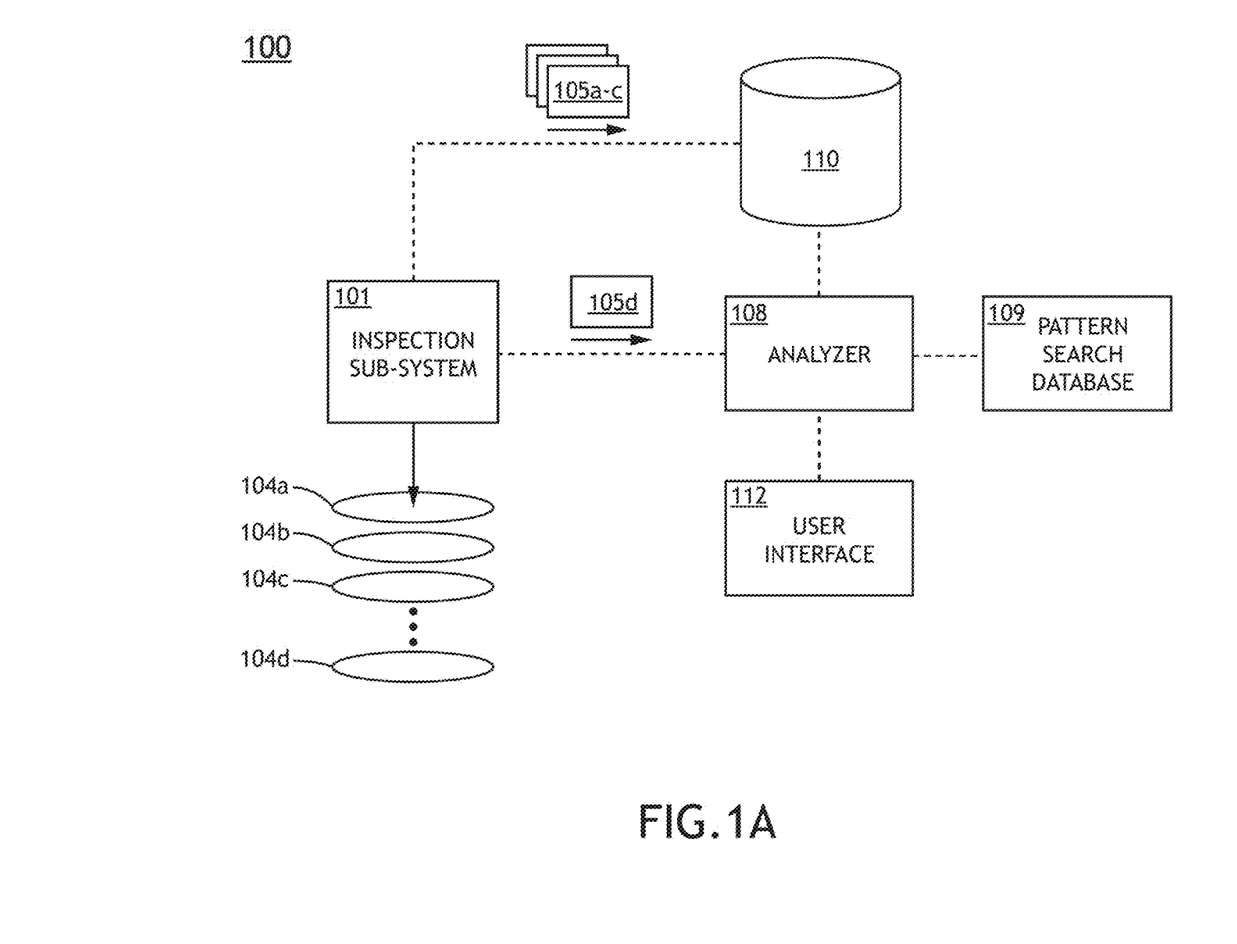
FIG. 1A is a block diagram view of a system for production line monitoring, in accordance with one or more embodiments of the present disclosure.

FIG. 1A illustrates a block diagram view of an inspection system 100, in accordance with one or more embodiments of the present disclosure. In one embodiment, the inspection system 100 serves as a semiconductor device production monitoring system to identify one or more device excursions during fabrication of a given semiconductor device.

In one embodiment, the system 100 includes an inspection sub-system 101. In one embodiment, the inspection sub-system 101 is configured to perform an inspection process on a set of samples 104a-104d. For example, the inspection sub-system 101 may include a wafer inspection sub-system 104a-104d for inspecting semiconductor wafers. As used throughout the present disclosure, the term "wafer" generally refers to substrates formed of a semiconductor and/or non-semiconductor material.

The inspection sub-system 101 may include an illumination source and one or more detectors for carrying out image acquisition. The illumination source is configured to generate illumination, which is then directed to and scanned across the sample surface by the inspection sub-system 101 (e.g., via illumination optics and sample stage). Further, the detector is configured to detect illumination that is reflected or scattered (or otherwise emitted) by the sample and generate an electronic signal indicative of the measured illumination signal. Details related to the optical configuration of the inspection sub-system 101 are provided further herein (e.g., FIGS. 3A-3C).

Figure 1B:
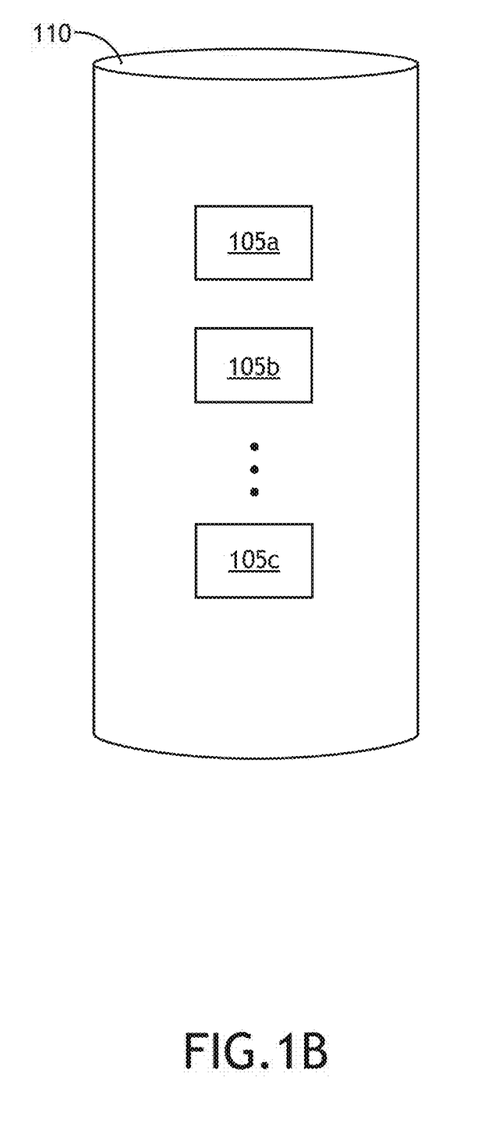
FIG. 1B is a conceptual view of a database for storing inspection results, in accordance with one or more embodiments of the present disclosure.

In another embodiment, the system 100 includes a database 110. In one embodiment, the database 110 is maintained in memory (e.g., local memory or remote memory). In one embodiment, the database 110 is communicatively coupled (e.g., wireline or wirelessly coupled) to the detector output of the inspection sub-system 101. For example, the inspection sub-system 101 may perform a reference set of scans on a reference set of samples 104a-104c and transmit the inspection results to the database 110. As shown in FIG. 1B, the results 105a-105c associated with these reference scans may be stored in the database 110.

In another embodiment, each inspection result from the reference set of samples 104a-104c includes a set of geometric pattern codes. Each geometric pattern code of a set of geometric pattern codes corresponds to one defect inspected by the inspection sub-system 101. For example, in the case where samples 104a, 104b, and/or 104c include N number of defects, the inspection results for this case may include N number of geometric pattern codes. Each geometric pattern code serves to identify a pattern associated with a particular defect of a given sample. In this sense, a geometric pattern code may act as a unique identifier or descriptor for unique patterns on a given sample. While the present disclosure focuses on the use of geometric pattern codes to identify each unique pattern associated with each defect, it is recognized herein that embodiments of the present disclosure may be extended to any systematic approach to identifying the unique pattern associated with each defect.

In another embodiment, a set of geometric pattern codes may be stored in the database 110 for each sample 104a-104c. For example, the inspection results 105a containing a set of geometric pattern codes associated with the inspection of sample 104a may be stored in database 110. By way of another example, the inspection results 105b containing a set of geometric pattern codes associated with the inspection of sample 104b may be stored in database 110. By way of another example, the inspection results 105c containing a set of geometric pattern codes associated with the inspection of sample 104c may be stored in database 110. In this regard, a historical database containing a set of geometric pattern codes for multiple samples 104a-104c may be built up. As discussed further herein, the database of results 105a-105c may be statistically aggregated and/or analyzed and can be used as reference, which inspection results for additional samples may be tested against.

Figure 1C:
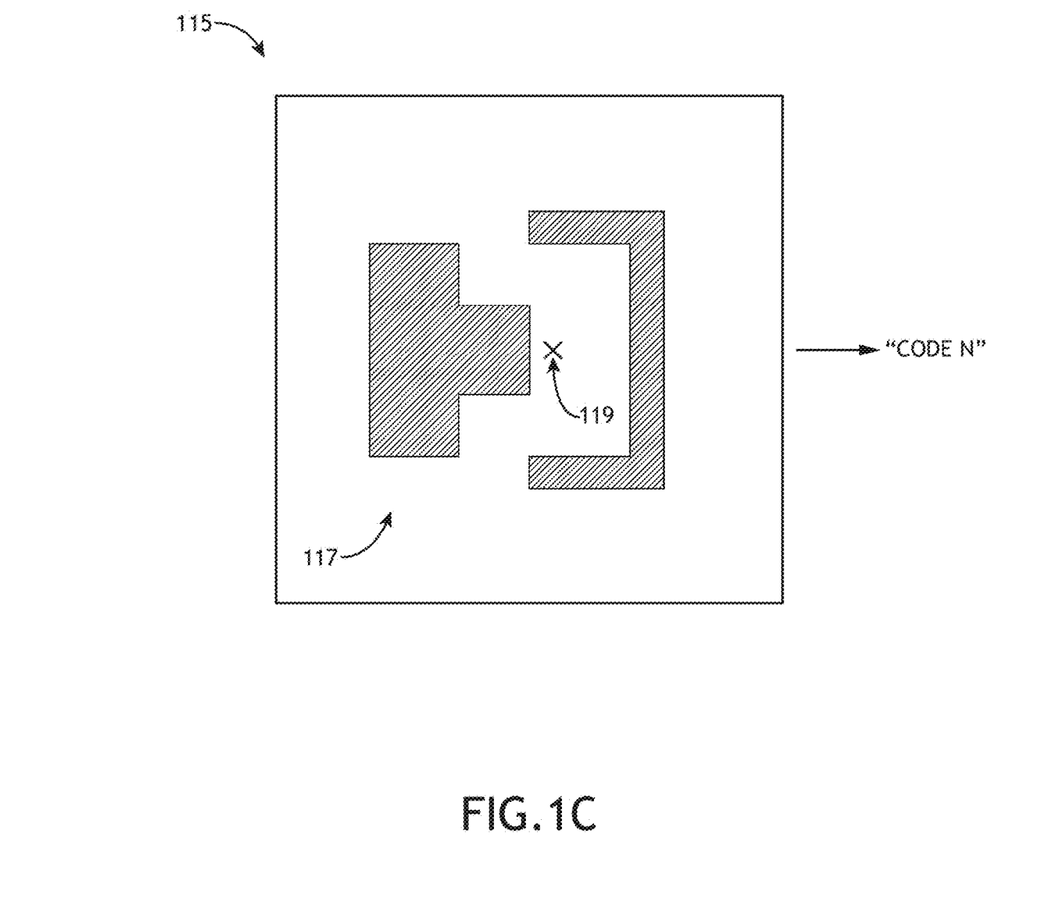
FIG. 1C is a conceptual view of a pattern and a corresponding geometric pattern code, in accordance with one or more embodiments of the present disclosure.

FIG. 1C illustrates a conceptual view of a unique pattern 117 and a defect 119 located on/in the pattern 117, in accordance with one or more embodiments of the present disclosure. In one embodiment, the unique pattern 117 may be identified by a unique identification code, or a geometric pattern code. For example, following acquisition of imagery data with the inspection sub-system 101, patterns present in the imagery data may be correlated with design data and assigned a corresponding geometric pattern code. In one embodiment, the geometric pattern code is a unique string that serves to identify the pattern associated (e.g., under, proximate to) with an identified defect. The geometric pattern codes for each of the defects identified in a given inspection scan may then be transmitted to and stored in database 110 for later analysis.

Figure 1D:
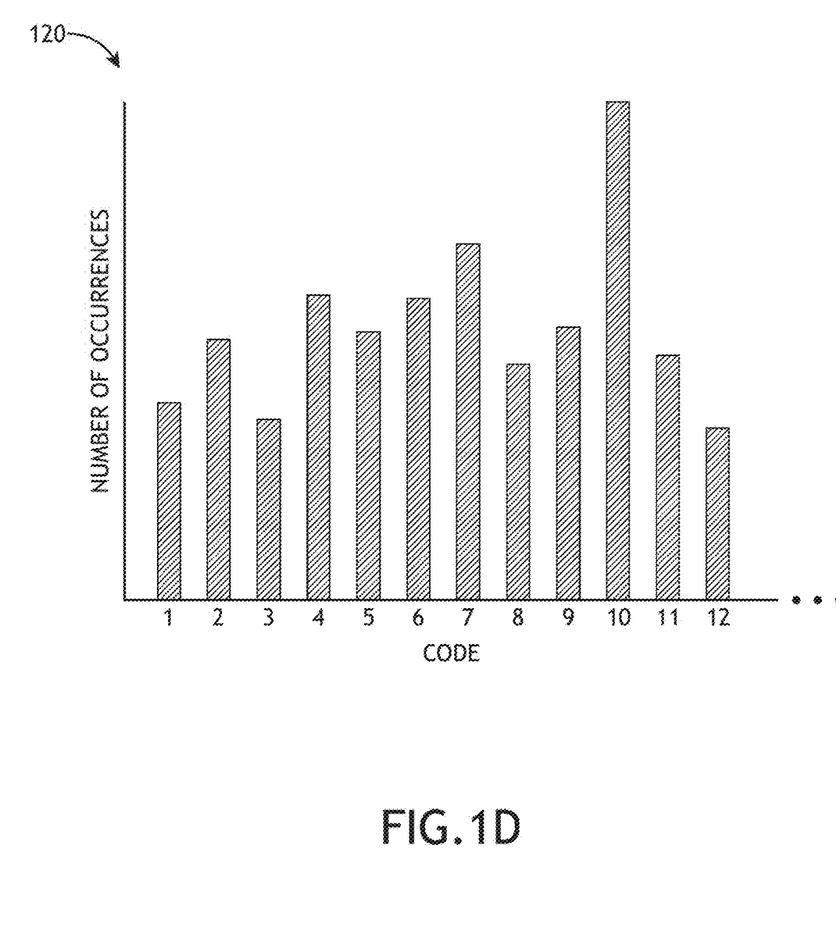
FIG. 1D is a conceptual view of histogram for tracking the frequency of geometric pattern codes, in accordance with one or more embodiments of the present disclosure.

FIG. 1D illustrates a histogram 120 used to visualized the frequency of each of a set of geometrical defect codes 1 through M, in accordance with one or more embodiments of the present disclosure. It is noted that histograms may be developed individually for each inspected sample or on an aggregated basis across samples.

It is noted that the geometric pattern codes may be generated utilizing any design data analysis technique. For example, the geometric pattern codes may be generated utilizing "design-based grouping." Design-based grouping is described generally in U.S. Pat. No. 7,570,796, issued on Aug. 4, 2009 to Zafar et al.; U.S. Pat. No. 7,676,077, issued on Mar. 9, 2010 to Kulkarni et al.; U.S. Pat. No. 8,041,103, issued on Oct. 18, 2011 to Kulkarni et al.; and U.S. Pat. No. 9,183,624, issued on Nov. 10, 2015 to Karsenti et al., which are each incorporated herein by reference in the entirety.

In another embodiment, system 100 includes an analyzer 108. The analyzer 108 may include one or more processors and memory. The one or more processors are configured to execute a set of program instructions maintained on the memory. In this regard, analyzer 108 may be programmed with one or more program instructions to execute one of more of the various data processing and/or control steps of the present disclosure. In one embodiment, the analyzer 108 is communicatively coupled to the output of the detector of the inspection sub-system 101. In this regard, the analyzer 108 may receive inspection results from the samples 104a-104d from inspection sub-system 101. In another embodiment, the analyzer 108 is communicatively coupled to the database 110, allowing the analyzer 108 to retrieve the historical inspection results 105a-105c accumulated in the database 110 (and allowing the analyzer 108 to update the database 110 with analysis results).

In one embodiment, the database 110 stores inspection results 105a-105c containing geometric pattern or codes for each of the defects in the inspection results 105a-105c from a reference set of samples 104a-104c. For example, as shown in FIG. 1A, the inspection sub-system 101 may perform an inspection process on a series of samples 104a-104c and then transmit those results (including the corresponding sets of geometric pattern or codes) to database 110. It is noted that the system 100 is not limited to the number of samples depicted in FIG. 1A, which is provided merely for illustrative purposes.

In another embodiment, the analyzer 108 is programmed to receive an additional inspection result (i.e., an Nth inspection result) acquired from an additional sample 104d (i.e., an Nth sample 104d) by the inspection sub-system 101. It is noted that the Nth inspection result 105d includes an Nth set of geometric pattern codes corresponding to the defects identified on the Nth sample. Additionally, the Nth inspection result 105d may also be transmitted to and stored in database 110. For the remainder of the present disclosure the additional inspection result and the additional sample are referred to herein as the Nth inspection result and the Nth additional sample respectively.

In another embodiment, the analyzer 108 is programmed to retrieve the inspection results 105a-105c from the database 110. For example, the analyzer 108 may retrieve the inspection results 105a-105c including the geometric pattern codes for the defects of each sample 104a-104c from the database 110.

In another embodiment, the analyzer 108 is programmed to correlate the set of geometric pattern codes of the Nth sample 104d with the geometric pattern codes from the reference set of samples 104a-104c. The analyzer 108 may carry out any statistical analysis technique known in the art to correlate or compare the set of geometric pattern codes of the Nth sample 104d with the geometric pattern codes from the reference set of samples 104a-104c. For example, the analyzer 108 may statistically aggregate or extract one or more characteristics of the inspection results 104a-104c retrieved from the database 110. For instance, the analyzer 108 may average the frequency of occurrence of each type of geometry defect code across the multiple samples.

In one embodiment, the correlation carried out by the analyzer 108 includes comparing the set of geometric pattern codes of the Nth sample 104d to the geometric pattern codes from the reference set of samples 104a-104c. In this regard, through the comparison, the analyzer 108 may identify a deviation between the set of geometric pattern codes of the Nth sample 104d and the geometric pattern codes from the reference set of samples 104a-104c. For example, the comparison may involve comparing a frequency of occurrence of each of the set of geometric pattern codes of the Nth sample 104d to the frequency of occurrence of the geometric pattern codes from the reference set of samples 104a-104c.

In another embodiment, following the comparison of the set of geometric pattern codes of the Nth sample 104d to the geometric pattern codes from the reference set of samples 104a-104c, the analyzer 108 may determine whether the measured deviation is larger than sample-to-sample variations or fluctuations present in the geometric pattern codes from the reference set of samples 104a-104c. For example, the analyzer 108 may measure or determine the deviation in the frequency of each of the geometric pattern codes between two or more of the reference samples 104a-104c. For instance, the analyzer 108 may determine the standard deviation in the frequency of each of the geometric pattern codes across the set of reference samples 104a-104c. In turn, the measured deviation in the geometric pattern codes across the reference samples 104a-104c may then be compared to the deviation between the geometric pattern codes of the Nth sample 104d and the reference samples 104a-104c. It is noted that such a comparison step may serve to assess the statistical significance of deviations between the geometric pattern codes of the Nth sample 104d and the reference samples 104a-104c It is noted that the comparison of historical geometric pattern codes from reference samples 104a-104c to the geometric pattern codes of the Nth sample 104d may be carried out in aggregated form, where the frequency of the geometric pattern codes from reference samples 104a-104c is aggregated and then compared to frequency of the geometric pattern codes of the Nth sample 104d. Alternatively, the comparison may be carried out at an individual sample level, where the frequency of the geometric pattern codes for each individual reference sample 104a-104c is compared to frequency of the geometric pattern codes of the Nth sample 104d. Such a sample-level comparison allows the analyzer 108 to track the time/sample evolution of pattern frequency.

Based on the correlation carried out by the analyzer 108, the analyzer 108 may identify one or more new patterns (not present in the historical database 110) and/or one or more patterns displaying a frequency of occurrence above a selected threshold (e.g., statistical process control (SPC) threshold). For instance, the analyzer 108 may compare the frequency of occurrence of each geometric pattern code present in the results 105a-105c to the frequency of occurrence of each geometric pattern code present in the Nth results 105d. Since the geometric pattern codes each serve to identify a unique pattern, with the above comparison, the analyzer 108 may identify potentially problematic patterns (patterns connected to a defect) in the Nth results 105d that have grown in frequency of occurrence relative to the reference results 105a-105c. Further, the analyzer 108 may identify new patterns in the Nth result 105d that were not present in the reference results 105a-105c. It is noted that the new or more frequently occurring patterns noted above are patterns that are cataloged with associated defect information via the accumulation of the geometric pattern codes, which are collected for each defect in a given scan. As a pattern (which is in close proximity to a defect) begins to emerge or deviate in frequency relative to historical data stored in database 110, this behavior may signal a systematic failing of the pattern.

In another embodiment, the analyzer 108 may flag the one or more new patterns and/or the one or more patterns displaying a frequency of occurrence above a selected threshold. For example, new patterns that emerge during the measurement of the Nth sample 105d may be flagged and stored in memory for future retrieval and analysis. By way of another example, new patterns that emerge during the measurement of the Nth sample 105d may be flagged and stored in memory. For instance, the one or more new patterns or the one or more patterns displaying a frequency of occurrence above a selected threshold may be flagged for later review and/or classification.

In another embodiment, the analyzer 108 may report an excursion alert in response to the identification of one or more new patterns and/or the one or more patterns displaying a frequency of occurrence above a selected threshold. For example, the analyzer 108 may transmit an excursion alert to a display of the user interface 112 for viewing by a user. By way of another example, the analyzer 108 may transmit an excursion alert to a control system of a production line for fabrication of the semiconductor devices of the samples 104a-104d.

In another embodiment, analyzer 108 may direct the inspection sub-system 101 (or another inspection tool or review tool) to inspect one or more defects associated with the one or more new patterns and/or the one or more patterns displaying a frequency of occurrence above a selected threshold found in the analysis steps above. In another embodiment, upon acquiring inspection data from the one or more defects associated with the one or more new patterns and/or the one or more patterns displaying a frequency of occurrence above a selected threshold, the analyzer 108 may export the sampled defect data to a defect image database (e.g., KLARF file).

In another embodiment, in response to the identification of one or more new patterns and/or the one or more patterns displaying a frequency of occurrence above a selected threshold, the analyzer 108 may transmit the learned information associated with the Nth sample 105d (and on) to the database 110. In this regard, the database 110 may continually be updated as new samples are analyzed by the analyzer 108. For instance, once the database 110 is updated with the data and analysis results associated with the Nth sample 105d, the analyzer 108 may then utilize the Nth sample 105d data as part of the historical data to then analyze the geometric pattern codes associated with the N+1 sample and so on.

In another embodiment, the system 100 includes a pattern search database 109. As shown in FIG. 1A, the pattern search database 109 may be communicatively coupled to the analyzer 108 (e.g., wireline or wireless connection). In one embodiment, the analyzer 108 may provide/transmit one or more new patterns identified by the analyzer 108 to the pattern search database 109. In another embodiment, the pattern search database 109 searches itself (or one or more other processors search the pattern search database 109) and identifies one or more instances of the one or more new patterns in the pattern search database 109. In another embodiment, the pattern search database 109 transmits the number of instances of the newly identified one or more patterns that appear in the pattern search database 109 to the analyzer 108. In turn, the analyzer 108 may correlate the number of instances of the one or more new patterns with a failure frequency of each geometric design code of the reference set of samples 104a-104c and the additional sample 104d stored in the database 110. In another embodiment, the analyzer 108 may flag one or more new patterns displaying a failure frequency above a selected threshold as a systematic defect.

Figure 1E:
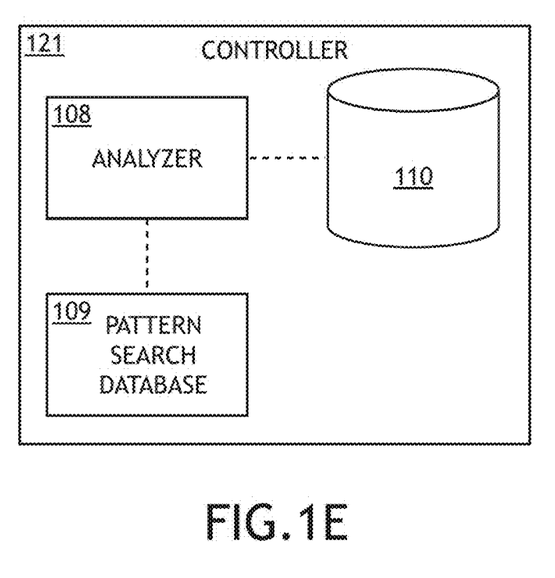
FIGS. 1E-F are block diagram views of a controller of a system for production line monitoring, in accordance with one or more embodiments of the present disclosure.
Figure 1F:
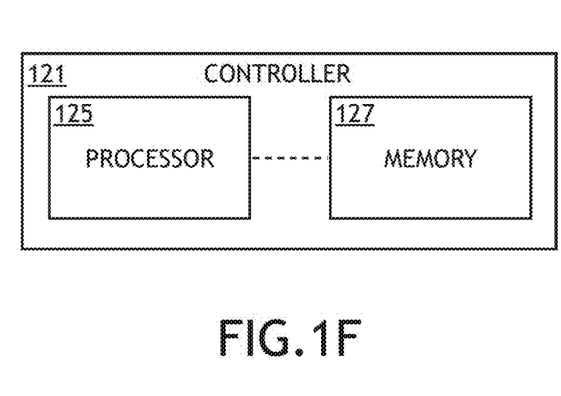

It is noted herein that the analyzer 108, pattern search database 109 and/or database 110 may be embodied in any number of topologies. In one embodiment, as shown in FIG. 1E, the analyzer 108, pattern searcher 109 and/or database 110 may all reside on a single controller 121. The controller 121 may include one or more processors 125 configured to execute program instructions maintained in memory 127. In this regard, the one or more processors 125 and program instructions may execute the various steps associated with the analyzer 108, pattern searcher 109 and/or database 110 described throughout the present disclosure. In this embodiment, the analyzer 108, pattern search database 109 and/or database 110 may be considered modules executed by the one or more processors 125.

In another embodiment, the analyzer 108, pattern search database 109 and/or database 110 may be arranged independent from one another, with each containing circuitry for executing their respective data handling functions. For example, the analyzer 108 exists as an independent analyzer unit or analyzer circuitry (e.g., processor, memory, communication circuitry, and etc.) configured to execute the various analyzer functions described throughout the present disclosure. Further, the pattern search database 109 exists as an independent pattern search unit or pattern search circuitry (e.g., processor, memory, communication circuitry, and etc.) configured to execute the various analyzer functions described throughout the present disclosure. Further, the database 110 exists as an independent database unit or database circuitry (e.g., processor, memory, communication circuitry, and etc.) configured to execute the various database functions described throughout the present disclosure. For example, the analyzer 108 and/or pattern search database 109 may include one or more computers communicatively coupled (e.g., via wireline or wireless connection) to the inspection sub-system 101. Additionally, the database 110 may consist of a remote database server, which is communicatively coupled (e.g., network connection) to the analyzer 108, pattern search database 109 and/or inspection sub-system 101.

In another embodiment, one or more of the analyzer 108, pattern seach database 109 and/or database 110 may reside on or near the inspection sub-system 101. For example, the analyzer 108 may be embodied on the inspection sub-system 101 (e.g., the inspection tool), which is then communicatively coupled to the database 110 and/or the pattern search database 109 through one of the various approaches described above.

The one or more processors of the various embodiments described above may include any one or more processing elements known in the art. The one or more processors may include any microprocessor-type device configured to execute software algorithms and/or instructions. In one embodiment, the one or more processors may include of a desktop computer, mainframe computer system, workstation, image computer, parallel processor, or other computer system (e.g., networked computer) configured to execute a program configured to operate the system 100, as described throughout the present disclosure. It should be recognized that the steps described throughout the present disclosure may be carried out by a single computer system or, alternatively, multiple computer systems. In general, the term "processor" may be broadly defined to encompass any device having one or more processing elements, which execute program instructions (e.g., module) from a non-transitory memory. Moreover, different subsystems of the system 100 (e.g., display, user interface, inspection sub-system) may include a processor or logic elements suitable for carrying out at least a portion of the steps described throughout the present disclosure. Therefore, the above description should not be interpreted as a limitation on the present invention but merely an illustration.

The memory may include any storage medium known in the art suitable for storing program instructions executable by the associated one or more processors and/or database information. For example, the memory may include, but is not limited to, a read-only memory, a random access memory, a magnetic or optical memory device (e.g., disk), a magnetic tape, a solid state drive and the like. In another embodiment, it is noted herein that the memory is configured to store one or more results from the inspection sub-system (e.g., database) and/or the output of the various steps described herein. It is further noted that memory may be housed in a common controller housing with the one or more processors. In another embodiment, the memory may be located remotely with respect to the physical location of the processors and controller. For instance, the one or more processors of the controller may access a remote memory (e.g., server), accessible through a network (e.g., internet, intranet and the like).

Figure 2:
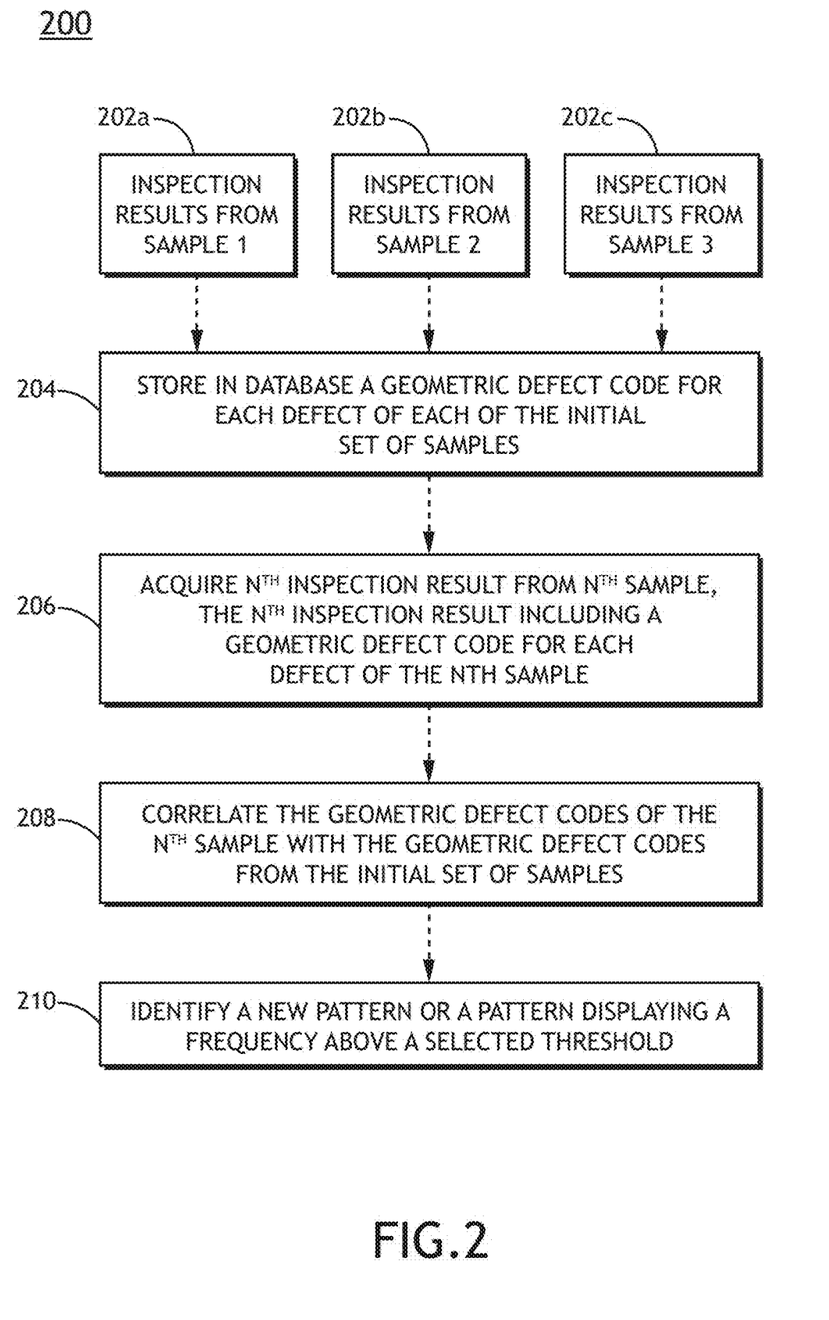
FIG. 2 is a flow diagram view depicting a method of production line monitoring, in accordance with one or more embodiments of the present disclosure.

FIG. 2 illustrates a process flow diagram 200 depicting a method of production monitoring, in accordance with one or more embodiments of the present disclosure.

In steps 202a-202c, inspection results from a first sample, a second sample and at least a third sample are acquired. For example, as shown in FIG. 1A, inspection sub-system 101 may scan samples 104a-104c and provide the associated inspection results 105a-105c to database 110. The samples 104a-104c may serve as initial or references samples, which serve as a reference to later inspected samples (e.g., Nth sample 104d).

In addition, each of the inspection results 105a-105c may contain a set of geometric pattern codes. Each of the geometric pattern codes in a given inspection result may serve to uniquely identify and/or describe a pattern (or portion of a pattern) on the given sample that is proximate to or underneath a detected defect.

It is noted that the system 100 and method 200 are not limited to three reference/initial samples and the later inspected Nth sample is not limited to a single sample. The reference/initial samples and the later inspected Nth sample have been illustrated as such merely for illustrative purposes.

In step 204, a geometric pattern code for each of the defects is stored in database 110 for each of the samples. For example, as shown in FIG. 1A, once the inspection results 105a-105c are received from the inspection sub-system 101 (e.g., from one or more detectors of the inspection sub-system 101) the database 110 may store them (e.g., stored in memory).

In step 206, inspection results from an Nth sample are acquired. For example, as shown in FIG. 1A, inspection sub-system 101 may scan an Nth sample 104d and provide the associated inspection results 105d to analyzer 108.

In step 208, the geometric pattern codes associated with the Nth sample 104d are correlated with the geometric pattern codes from the reference set of samples 104a-104c. For example, as shown in FIG. 1A, the analyzer 108 may retrieve the geometric pattern codes associated with the reference samples 104a-104c from database 110. Then, the analyzer 108 may compare the geometric pattern codes associated with the Nth sample 104d to the geometric pattern codes from the reference set of samples 104a-104c. The comparison may be carried out in any manner described previously herein. For instance, the analyzer 108 may compare the frequency of occurrence of each of the geometric pattern codes associated with the Nth sample 104d to the frequency of occurrence of each of the geometric pattern codes from each of the reference set of samples 104a-104c. Such a comparison can be carried out in statistically aggregated manner or a sample-by-sample basis.

In step 210, based on the correlation step of 208, a new pattern or a pattern displaying a frequency of occurrence above a selected threshold is identified. For example, as shown in FIG. 1A, the analyzer 108 may identify any new pattern represented by the geometric pattern codes of Nth sample 104d that was not present in the data associated with samples 104a-104c. By way of another example, as shown in FIG. 1A, the analyzer 108 may identify any pattern represented by the geometric pattern codes of Nth sample 104d that displays a frequency of occurrence larger than a selected frequency threshold. In one instance, the selected frequency threshold may include the frequency of occurrence of the same pattern in the data associated with samples 104a-104c. In another instance, the selected frequency threshold may include a frequency of occurrence selected by a user. It is further noted that method 200 may be extended to identify any frequency of occurrence within the geometric pattern code data that deviates or is unusual relative the geometric pattern code data of the initial/reference samples 104a-104c.

It is further contemplated that each of the embodiments of the method described above may include any other step(s) of any other method(s) described herein. In addition, each of the embodiments of the method described above may be performed by any of the systems described herein.

All of the methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. Furthermore, the results may be stored "permanently," "semi-permanently," temporarily, or for some period of time. For example, the storage medium may be random access memory (RAM), and the results may not necessarily persist indefinitely in the storage medium.

Referring again to FIG. 1A, the inspection sub-system 101 may take on any inspection configuration known in the art of sample inspection.

Figure 3A:
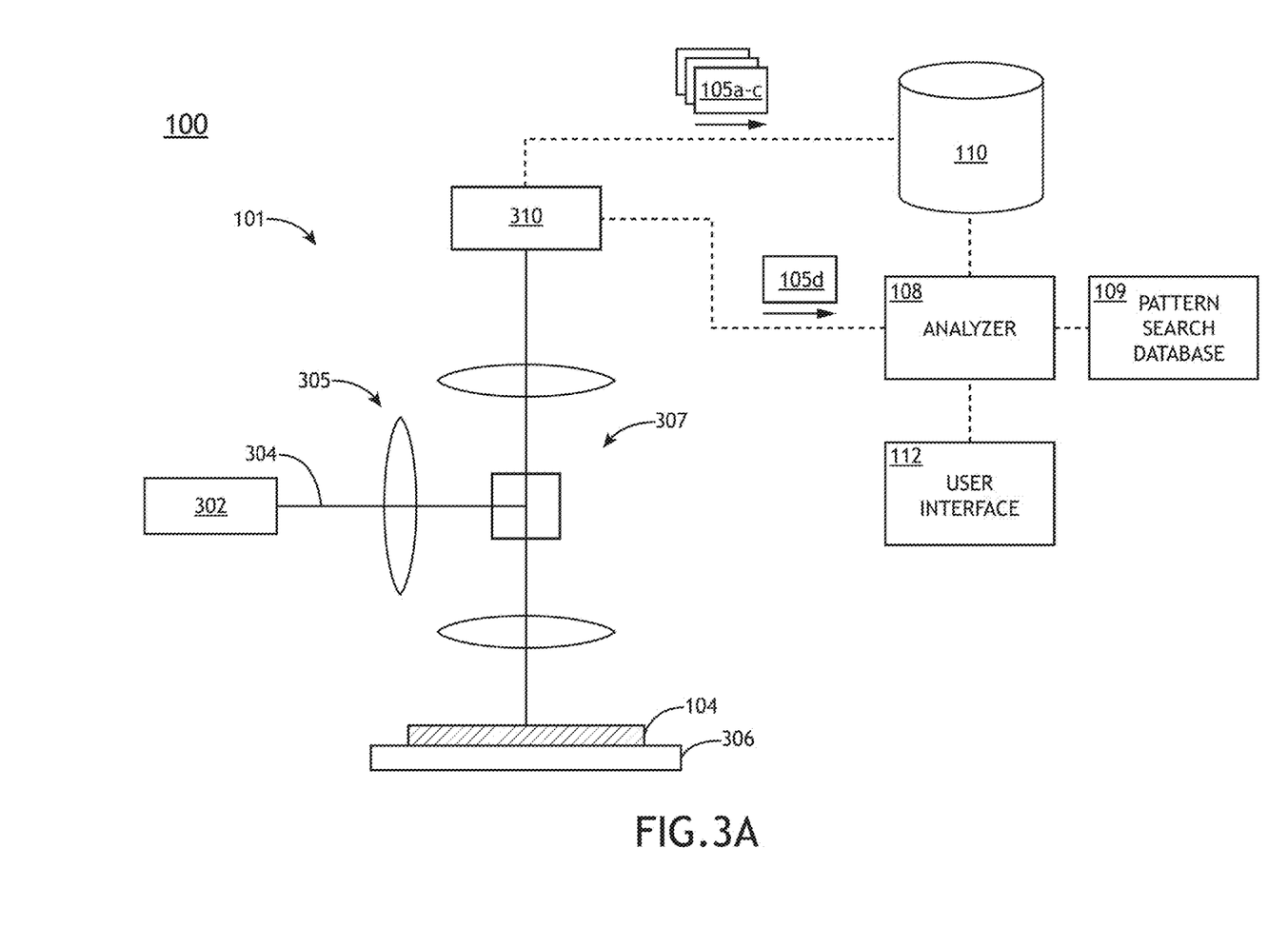
FIG. 3A is a block diagram view of a system in a brightfield configuration for production line monitoring, in accordance with one or more embodiments of the present disclosure.
Figure 3B:
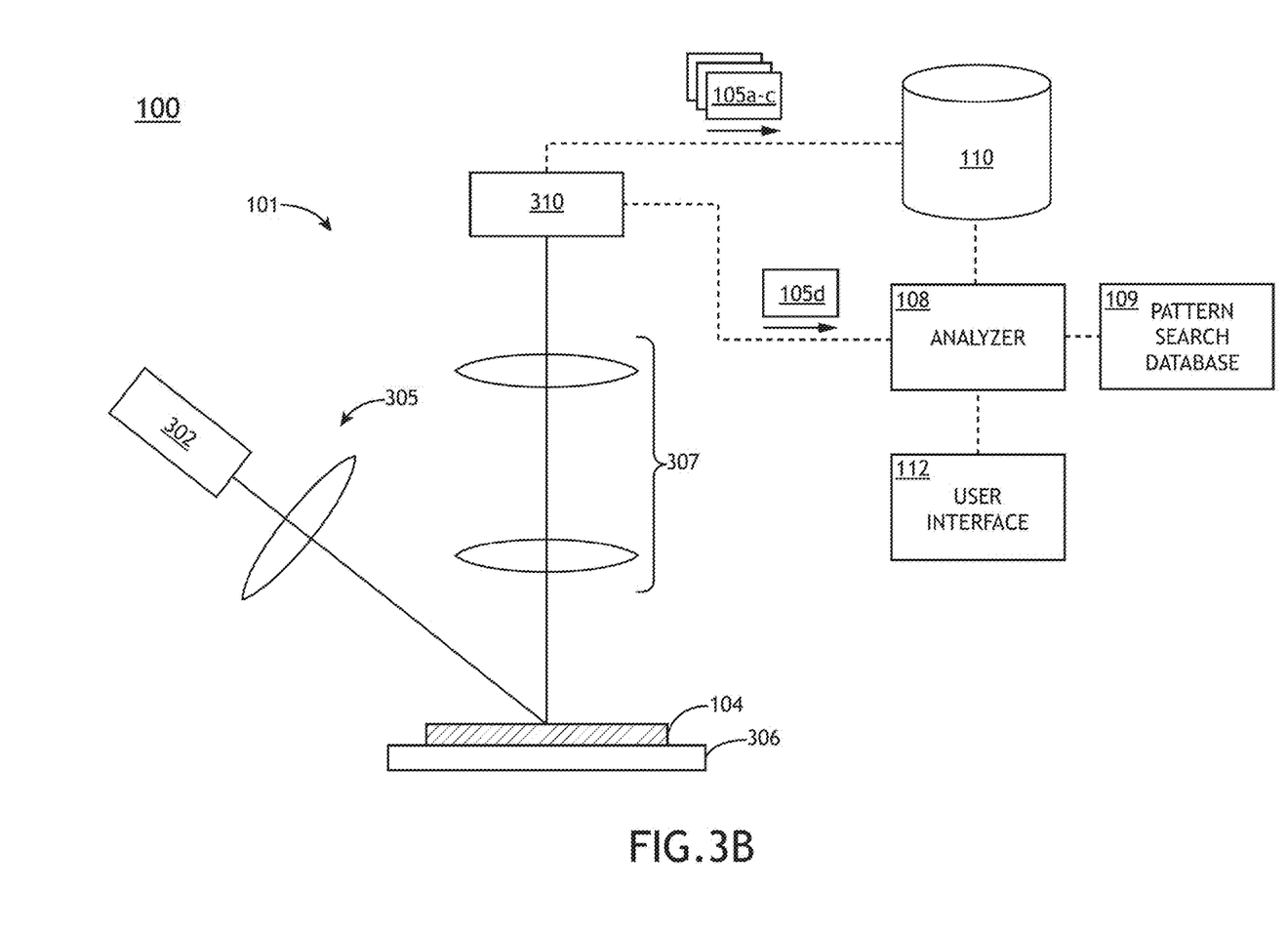
FIG. 3B is a block diagram view of a system in a darkfield configuration for production line monitoring, in accordance with one or more embodiments of the present disclosure.

FIG. 3A illustrates the inspection system 100 arranged in a brightfield inspection configuration, in accordance with one or more embodiments of the present disclosure. FIG. 3B illustrates the inspection system 100 arranged in a darkfield inspection configuration, in accordance with one or more embodiments of the present disclosure.

As shown in FIGS. 3A and 3B, the inspection sub-system 101 includes an illumination source 302 configured to emit illumination 304. The illumination source 302 may include any illumination source known in the art of inspection. For example, the illumination source 302 may include a broadband light source. For instance, the illumination source 302 may include, but is not limited to, a broadband plasma (BBP) source. In another instance, the illumination source 302 may include, but is not limited to, a supercontinuum laser source. By way of another example, the illumination source 302 may include a narrowband light source. For instance, the illumination source 302 may include, but is not limited to, one or more lasers.

In addition, the inspection sub-system 101 includes one or more detectors 310 for detecting/measuring illumination that is reflected, scattered or diffracted from the sample 104. For example, the one or more detectors 310 may include, but are not limited to, a CCD detector, a TDI-CCD detector, a PMT detector and the like. The one or more detectors 310 are communicatively coupled to the analyzer 108 and/or database 110 (or a controller containing the analyzer 108 and/or database 110). Further, the inspection sub-system 101 includes an illumination arm 305 and a collection arm 307. The illumination arm 305 may include any one or more optical elements known in the art for focusing, directing, filtering or process illumination 304, such as, but not limited to, lenses, mirrors, filters, beam splitters and the like. Additionally, the collection arm 307 may include any one or more optical elements known in the art for focusing, directing, filtering or process illumination 304, such as, but not limited to, lenses, mirrors, filters, beam splitters and the like. In another embodiment, the inspection sub-system 101 includes a sample stage 306 for securing and scanning the sample 104 relative to the beam of illumination 304.

Figure 3C:
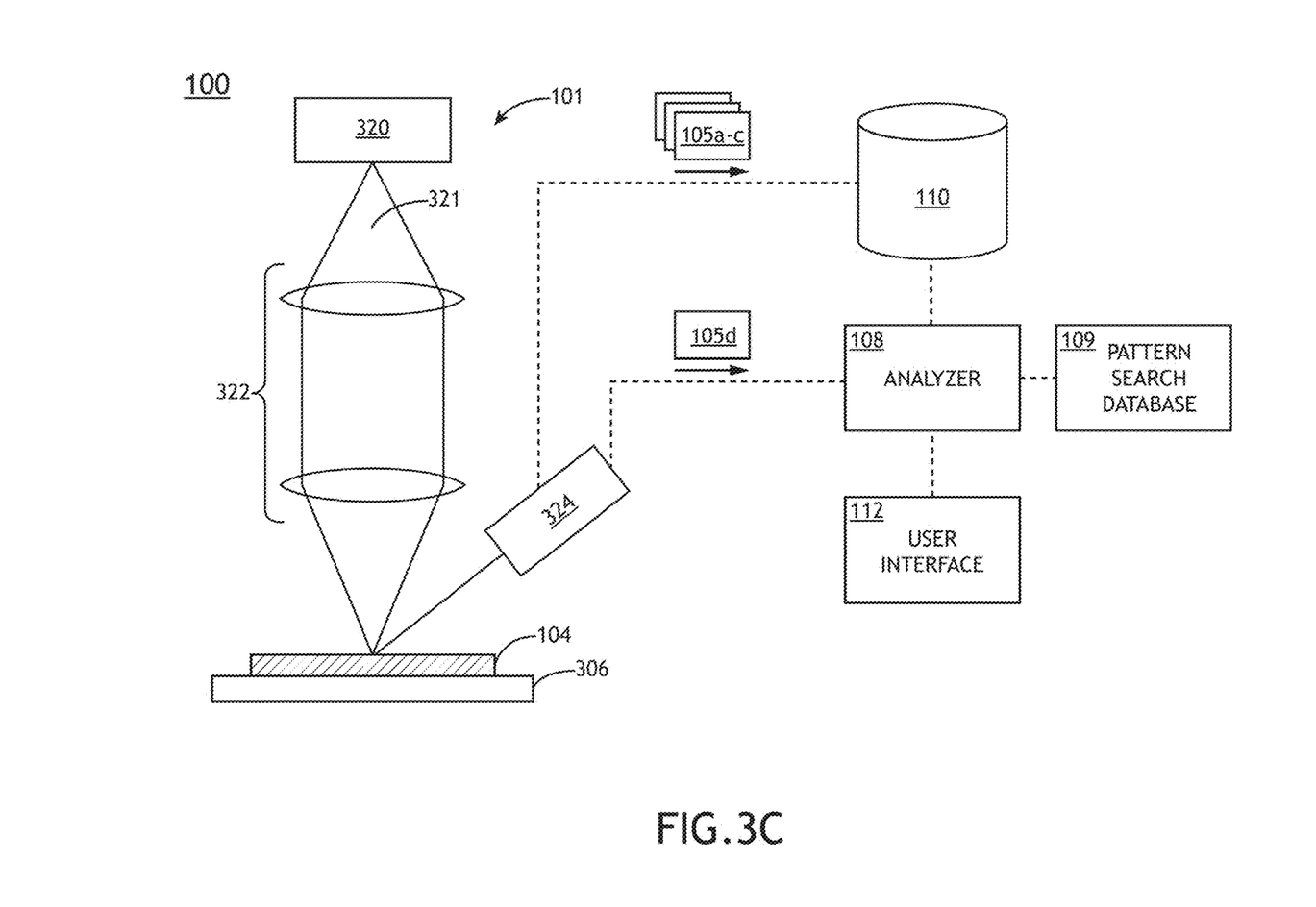
FIG. 3C is a block diagram view of an electron-beam based system for production line monitoring, in accordance with one or more embodiments of the present disclosure.

FIG. 3C illustrates the inspection system 100 arranged in an electron-beam inspection configuration, in accordance with one or more embodiments of the present disclosure. The electron-beam configuration of the inspection sub-system 101 may take on any configuration known in the art of electron-beam inspection. As shown in FIG. 3C, the inspection sub-system 101 includes an electron source 320 configured to emit one or more electron beams 321. The electron beam source 320 may include any electron-beam source known in the art of inspection. For example, the electron beam source may include an electron gun.

In addition, the inspection sub-system 101 includes one or more detectors 324 for detecting/measuring an electron signal that emanates from the surface of the sample 104. For example, the one or more detectors 324 may include, but are not limited to, a secondary electron detector and/or a backscattered electron detector.

The one or more detectors 324 are communicatively coupled to the analyzer 108 and/or database 110 (or a controller containing the analyzer 108 and/or database 110). Further, the inspection sub-system 101 includes an electron-optical column 322. The electron-optical column 322 may include any one or more electron-optical elements known in the art for focusing, directing, filtering or processing the electron beam 321, such as, but not limited to, a condenser lenses, objective lenses, scanning coils, beam deflectors and the like. In another embodiment, the inspection sub-system 101 includes a sample stage 306 for securing and scanning the sample 104 relative to the electron beam 321.

Referring again to FIG. 1A, in another embodiment, the system 100 includes a user interface 112. The user interface 112 may include any user interface known in the art. For example, the user interface 112 may include a user input device and/or a display for displaying data to a user and receiving user input instructions. For example, the user input device may include, but is not limited to, a keyboard, a keypad, a touchscreen, a lever, a knob, a scroll wheel, a track ball, a switch, a dial, a sliding bar, a scroll bar, a slide, a handle, a touch pad, a paddle, a steering wheel, a joystick, a bezel input device or the like. The display device may include any display device known in the art. In one embodiment, the display device may include, but is not limited to, a liquid crystal display (LCD). In another embodiment, the display device may include, but is not limited to, an organic light-emitting diode (OLED) based display. In another embodiment, the display device may include, but is not limited to a CRT display. In a general sense, any display device capable of integration with a user interface device (e.g., touchscreen, bezel mounted interface, keyboard, mouse, trackpad, and the like) is suitable for implementation in the present invention. In the case of a touchscreen interface device, those skilled in the art should recognize that a large number of touchscreen interface devices may be suitable for implementation in the present invention. For instance, the display device may be integrated with a touchscreen interface, such as, but not limited to, a capacitive touchscreen, a resistive touchscreen, a surface acoustic based touchscreen, an infrared based touchscreen, or the like. In a general sense, any touchscreen interface capable of integration with the display portion of the display device is suitable for implementation in the present invention.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors. A typical data processing system may be implemented utilizing any suitable commercially available components, such as those typically found in data computing and/or communication and/or network computing and/or communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein.

Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

What is claimed:

1. A system for semiconductor device production monitoring comprising:
    an inspection sub-system including an illumination source and a detector, wherein the illumination source is configured to generate illumination, wherein the inspection sub-system is configured to scan the illumination from the illumination source across a sample, wherein the detector is configured to detect illumination from the sample;
    a database maintained in memory for storing inspection results acquired from a reference set of samples with the inspection sub-system, wherein each inspection result from the reference set of samples includes a geometric pattern code for each defect identified on a particular reference sample, wherein the geometric pattern code serves to identify the pattern associated with a particular defect on the particular reference sample; and
    an analyzer, the analyzer including one or more processors and memory, wherein the one or more processors are configured to execute a set of program instructions maintained on the memory, the program instructions configured to cause the one or more processors to:
        receive an additional inspection result from an additional sample from the inspection sub-system, wherein the additional inspection result includes an additional set of geometric pattern codes for each defect identified within the additional inspection result from the additional sample;
        retrieve the inspection results acquired from the reference set of samples including the geometric pattern code for each defect identified on the particular reference sample from the database; and
        correlate the set of geometric pattern codes of the additional sample with the geometric pattern codes from the reference set of samples to identify at least one of one or more new patterns or one or more patterns displaying a frequency of occurrence above a selected threshold.

2. The system of claim 1, wherein the correlating the set of geometric pattern codes of the additional sample with the geometric pattern codes from the reference set of samples to identify at least one of one or more new patterns or one or more patterns displaying a frequency of occurrence above a selected threshold comprises:
    correlating a frequency of occurrence of each of the set of geometric pattern codes of the additional sample to the frequency of occurrence of each of the set of geometric pattern codes from the reference set of samples to identify at least one of one or more new patterns or one or more patterns displaying a frequency of occurrence above a selected threshold.

3. The system of claim 1, wherein the correlating the set of geometric pattern codes of the additional sample with the geometric pattern codes from the reference set of samples to identify at least one of one or more new patterns or one or more patterns displaying a frequency of occurrence above a selected threshold comprises:
    comparing the set of geometric pattern codes of the additional sample to the geometric pattern codes from the reference set of samples to identify a deviation between the set of geometric pattern codes of the additional sample and the geometric pattern codes from the reference set of samples; and
    determining whether the deviation is larger than sample-to-sample variations of the geometric pattern codes from the reference set of samples.

4. The system of claim 1, wherein the analyzer is further configured to:
flag at least one of the one or more new patterns or the one or more patterns displaying a frequency of occurrence above a selected threshold.

5. The system of claim 1, wherein the analyzer is further configured to:
report an excursion alert to a user interface in response to the identification of at least one of one or more new patterns or one or more patterns displaying a frequency of occurrence above a selected threshold.

6. The system of claim 1, wherein the analyzer is further configured to:
direct the inspection sub-system to perform one or more inspection measurements on one or more defects associated with at least one of the one or more new patterns or the one or more patterns displaying a frequency of occurrence above a selected threshold.

7. The system of claim 1, wherein the analyzer is further configured to:
provide an identified one or more new patterns to a pattern search database.

8. The system of claim 7, wherein the pattern search database is configured to identify one or more instances of the one or more new patterns in the pattern search data base.

9. The system of claim 8, wherein the pattern search database is configured to transmit the number of instances of the one or more new patterns appearing in the pattern search database to the analyzer.

10. The system of claim 9, wherein the analyzer is configured to correlate the number of instances of the one or more new patterns with a failure frequency of each geometric design code of the reference set of samples and the additional sample stored in the database.

11. The system of claim 10, wherein the analyzer is configured to flag one or more new patterns displaying a failure frequency above a selected threshold as a systematic defect.

12. The system of claim 1, wherein the inspection sub-system is configured in a brightfield inspection mode.

13. The system of claim 1, wherein the inspection sub-system is configured in a darkfield inspection mode.

14. The system of claim 1, wherein the inspection sub-system comprises:
a light-based inspection sub-system.

15. The system of claim 1, wherein the inspection sub-system comprises:
an electron-based inspection sub-system.

16. The system of claim 1, wherein the inspection sub-system comprises:
a narrow band inspection sub-system.

17. The system of claim 1, wherein the inspection sub-system comprises:
a broadband inspection sub-system.

18. The system of claim 17, wherein the broadband inspection sub-system comprises:
a broadband plasma (BPP) inspection sub-system.

19. The system of claim 1, wherein the sample comprises:
a semiconductor wafer.

20. A method for semiconductor device production monitoring comprising:
acquiring, with an illumination source and a detector of an inspection sub-system, a plurality of inspection results from a plurality of reference samples, each inspection result being acquired from one reference sample of the plurality of reference samples, wherein each inspection result includes a geometric pattern code for each defect identified on the particular reference sample, wherein the geometric pattern code serves to identify the pattern associated with the particular defect;
storing the acquired inspection results and the associated geometric pattern codes in a database;
acquiring, with the illumination source and the detector of the inspection sub-system, an additional inspection result from an additional sample, wherein the additional inspection result includes an additional set of geometric pattern codes for identifying each defect identified within the additional inspection result from the additional sample;
correlating, with one or more processors, the set of geometric pattern codes of the additional sample with the geometric pattern codes from the reference set of samples to identify at least one of one or more new patterns or one or more patterns displaying a frequency of occurrence above a selected threshold; and
directing the inspection sub-system to perform one or more inspection measurements on one or more defects associated with at least one of the one or more new patterns or the one or more patterns displaying a frequency of occurrence above a selected threshold.

21. The method of claim 20, wherein the correlating the set of geometric pattern codes of the additional sample with the geometric pattern codes from the reference set of samples to identify at least one of one or more new patterns or one or more patterns displaying a frequency of occurrence above a selected threshold comprises:
correlating a frequency of occurrence of each of the set of geometric pattern codes of the additional sample to the frequency of occurrence of each of the set of geometric pattern codes from the reference set of samples to identify at least one of one or more new patterns or one or more patterns displaying a frequency of occurrence above a selected threshold.

22. The method of claim 20, wherein the correlating the set of geometric pattern codes of the additional sample with the geometric pattern codes from the reference set of samples to identify at least one of one or more new patterns or one or more patterns displaying a frequency of occurrence above a selected threshold comprises:
comparing a frequency of occurrence the set of geometric pattern codes of the additional sample to the geometric pattern codes from the reference set of samples to identify a deviation between the set of geometric pattern codes of the additional sample and the geometric pattern codes from the reference set of samples; and
determining whether the deviation is larger than sample-to-sample variations of the geometric pattern codes from the reference set of samples.

23. The method of claim 20, further comprising:
flagging the one or more patterns displaying at least one of one or more new patterns or one or more patterns displaying a frequency of occurrence above a selected threshold.

24. The method of claim 20, further comprising:
reporting an excursion alert to a user interface in response to at least one of the one or more new patterns or one or more patterns displaying a frequency of occurrence above a selected threshold.

25. The method of claim 20, further comprising:
performing a pattern search on one or more new patterns to identity one or more instances of the one or more new patterns in the database.

26. A system for semiconductor device production monitoring comprising:

an inspection sub-system including an illumination source and a detector, wherein the illumination source is configured to generate illumination, wherein the inspection sub-system is configured to scan the illumination from the illumination source across a sample, wherein the detector is configured to detect illumination from the sample; and a controller, the controller including one or more processors and memory, wherein the one or more processors are configured to execute a set of program instructions maintained on the memory, the program instructions configured to cause the one or more processors to:

store inspection results acquired from a reference set of samples with the inspection sub-system, wherein each inspection result from the reference set of samples includes a geometric pattern code for each defect identified on a particular reference sample, wherein the geometric pattern code serves to identify the pattern associated with a particular defect on the particular reference sample;

receive an additional inspection result for an additional sample from the inspection sub-system, wherein the additional inspection result includes an additional set of geometric pattern codes for each defect identified within the additional inspection result from the additional sample; and correlate the set of geometric pattern codes of the additional sample with the geometric pattern codes from the reference set of samples to identify at least one of one or more new patterns or one or more patterns displaying a frequency of occurrence above a selected threshold.

* * * * *